(12) United States Patent
Perkins et al.

(10) Patent No.: US 11,850,173 B2
(45) Date of Patent: *Dec. 26, 2023

(54) FEMORAL AORTIC ACCESS MODULAR STENT ASSEMBLY AND METHOD

(71) Applicant: Medtronic Vascular, Inc., Santa Rosa, CA (US)

(72) Inventors: Keith Perkins, Santa Rosa, CA (US); Zachary Borglin, Santa Rosa, CA (US); Mark Stiger, Santa Rosa, CA (US); Julie Benton, Santa Rosa, CA (US); Steven Claessens, Santa Rosa, CA (US); Travis Rowe, Santa Rosa, CA (US); Mark Young, Santa Rosa, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/362,644

(22) Filed: Jun. 29, 2021

(65) Prior Publication Data
US 2021/0322188 A1    Oct. 21, 2021

Related U.S. Application Data

(63) Continuation of application No. 16/367,922, filed on Mar. 28, 2019, now Pat. No. 11,083,605.

(51) Int. Cl.
*A61F 2/07* (2013.01)
*A61F 2/852* (2013.01)
(Continued)

(52) U.S. Cl.
CPC ............. *A61F 2/90* (2013.01); *A61F 2/07* (2013.01); *A61F 2/852* (2013.01); *A61F 2/856* (2013.01);
(Continued)

(58) Field of Classification Search
CPC ...... A61F 2/07; A61F 2/89; A61F 2/90; A61F 2/852; A61F 2/856; A61F 2/954;
(Continued)

(56) References Cited

U.S. PATENT DOCUMENTS 6,102,940 A    8/2000   Robichon et al.
6,641,606 B2   11/2003  Ouriel et al.
(Continued)

FOREIGN PATENT DOCUMENTS

EP    2525742 B1   11/2012
EP    2574306 A1    4/2013
(Continued)

OTHER PUBLICATIONS

PCT/US2020/039169, The International Search Report and the Written Opinion of the International Searching Authority, dated Oct. 5, 2020, 16 pages.
(Continued)

*Primary Examiner* — Dinah Baria
(74) *Attorney, Agent, or Firm* — Brooks Kushman P.C.

(57) ABSTRACT

The techniques of this disclosure generally relate to a modular stent device that is deployed into the ascending aorta via femoral access. The modular stent device is a base or anchor component to which additional modular stent devices can be attached to exclude diseased areas of the aorta while at the same time allowing perfusion of the brachiocephalic artery, the left common carotid artery, and/or the left subclavian artery.

12 Claims, 12 Drawing Sheets

(51) Int. Cl.

| | |
|---|---|
| *A61F 2/856* | (2013.01) |
| *A61F 2/90* | (2013.01) |
| *A61F 2/89* | (2013.01) |
| A61F 2/954 | (2013.01) |
| A61F 2/06 | (2013.01) |

(52) U.S. Cl.
CPC ............... *A61F 2/89* (2013.01); *A61F 2/954* (2013.01); *A61F 2002/061* (2013.01); *A61F 2002/065* (2013.01)

(58) Field of Classification Search
CPC .......... A61F 2002/061; A61F 2002/065; A61F 2002/067
See application file for complete search history.

(56) References Cited

U.S. PATENT DOCUMENTS

| | | |
|---|---|---|
| 6,723,116 B2 | 4/2004 | Taheri |
| 6,814,752 B1 | 11/2004 | Chuter |
| 7,267,685 B2 | 9/2007 | Butaric et al. |
| 8,545,549 B2 | 10/2013 | Hartley et al. |
| 8,702,791 B2 | 4/2014 | Kelly |
| 8,734,504 B2 | 5/2014 | Kelly |
| 9,011,517 B2 | 4/2015 | Hartley et al. |
| 9,101,456 B2 | 8/2015 | Hartley et al. |
| 9,283,068 B2 | 3/2016 | Kelly |
| 9,370,413 B2 | 6/2016 | Kelly |
| 9,393,102 B2 | 7/2016 | Kelly |
| 9,592,112 B2 | 3/2017 | Arbefeuille et al. |
| 9,839,542 B2 | 12/2017 | Bruszewski et al. |
| 9,861,505 B2 | 1/2018 | Khoury |
| 9,949,818 B2 | 4/2018 | Kelly |
| 9,980,832 B2 | 5/2018 | Kelly |
| 9,993,330 B2 | 6/2018 | Roeder |
| 10,231,822 B2 | 3/2019 | Hartley |
| 2002/0058986 A1 | 5/2002 | Landau et al. |
| 2002/0099441 A1 | 7/2002 | Dehdashtian |
| 2003/0130720 A1 | 7/2003 | Depalma et al. |
| 2004/0117003 A1 | 6/2004 | Ouriel et al. |
| 2005/0102018 A1 | 5/2005 | Carpenter et al. |
| 2006/0155363 A1 | 7/2006 | LaDuca et al. |
| 2006/0184228 A1 | 8/2006 | Khoury |
| 2007/0168013 A1 | 7/2007 | Douglas |
| 2007/0250154 A1 | 10/2007 | Greenberg et al. |
| 2008/0097578 A1 | 4/2008 | Erickson et al. |
| 2008/0147173 A1 | 6/2008 | Mciff et al. |
| 2009/0043373 A1 | 2/2009 | Arnault de la Menardiere |
| 2009/0125100 A1 | 5/2009 | Mead |
| 2009/0306763 A1 | 12/2009 | Roeder et al. |
| 2010/0100168 A1 | 4/2010 | Chuter et al. |
| 2011/0196477 A1 | 8/2011 | Ganesan et al. |
| 2011/0238160 A1 | 9/2011 | Molony |
| 2012/0123527 A1 | 5/2012 | Isch |
| 2012/0271401 A1 | 10/2012 | Bruszewski et al. |
| 2013/0013050 A1 | 1/2013 | Shalev et al. |
| 2013/0013052 A1 | 1/2013 | Christiansen et al. |
| 2013/0274861 A1 | 10/2013 | Kelly |
| 2015/0157446 A1 | 6/2015 | Kelly |
| 2016/0287376 A1 | 10/2016 | Kelly |
| 2016/0324626 A1 | 11/2016 | Kelly |
| 2016/0367353 A1 | 12/2016 | Kelly |
| 2017/0296324 A1 | 10/2017 | Argentine |
| 2017/0340461 A1 | 11/2017 | Varga |
| 2018/0071077 A1 | 3/2018 | Argentine et al. |
| 2018/0153677 A1 | 6/2018 | Perkins et al. |
| 2018/0235786 A1 | 8/2018 | Kelly |
| 2018/0243076 A1 | 8/2018 | Greenberg et al. |
| 2018/0325653 A1 | 11/2018 | Kelly |
| 2019/0380851 A1 | 12/2019 | Bertini et al. |

FOREIGN PATENT DOCUMENTS

| | | |
|---|---|---|
| EP | 3448313 B1 | 4/2020 |
| WO | 2014163957 A1 | 10/2014 |
| WO | 2019245624 A1 | 12/2019 |

OTHER PUBLICATIONS

PCT/US2020/044833, The International Search Report and the Written Opinion of the International Searching Authority, dated Nov. 16, 2020, 11 pages.

M. Lachat, "Nexus aortic arch stentgraft: Mid-term results", Leipzig Interventional Course 2017, UniversitatsSpital Zurich, Jan. 24-27, 2017, pp. 1-30, www.leipzig-interventional-course.com.

Jae Woong Lim et al., "Totally endocascular aortic arch repair by branched stent graft placement", Journal of Vascular Surgery Cases, Dec. 2015, pp. 279-282, vol. 1, No. 4.

W. Anthony Lee, Md., "The Bolton Medical Branched Thoracic Stent-Graft", Sponsored by Bolton Medical, Inc., pp. 1-6.

Michael D. Dake et al., "Thoracic Branch Endoprosthesis: Early Case Experience and the Clinical Trial", Supplement to Endovascular Today, Mar. 2017, pp. 21-24, vol. 16, No. 3.

Augusto D'Onofrio et al., "Endovascular treatment of aortic arch aneurysm with a single-branched double-stage stent graft", The Journal of Thoracic and Cardiovascular Surgery, Jul. 11, 2017, pp. e75-e77, vol. 154, No. 5.

Joseph Anderson, "Complete endovascular debranching of the aortic arch: A report of two cases", Vascular, Jul. 11, 2014, pp. 1-7, http://vas.sagepub.com/conten1/early/2014/07/11/1708538114542174, SAGE Publications.

Ciro Ferrer et al., "Endovascular repair of aortic arch disease with double inner branched thoracic stent graft: the Bolton perspective", The Journal of Cardiovascular Surgery, Aug. 2018, pp. 547-553, vol. 59 No. 4.

Stephan Haulon et al., "Global experience with an inner branched arch endograft", The Journal of Thoracic and Cardiovascular Surgery, 2014, pp. 1709-1716, vol. 148 No.4.

Chen Huang et al., "Application of Unibody Single-Branch Endografts in Stanford Type B Dissections with Primary Entry Tear Adjacent to the Left Subclavian Artery: A Computed TomographyeBased Planning Study", Annals for Vascular Surgery, Aug. 2015, pp. 1174-1180, vol. 29 No. 6.

Himanshu J. Patel et al., "Branched Endovascular Therapy of the Distal Aortic Arch: Preliminary Results of the Feasibility Multicenter Trial of the Gore Thoracic Branch Endoprosthesis", Branched Aortic Arch Tevar Trial, The Society of Thoracic Surgeons, Mar. 22, 2016, pp. 1190-1198, Elsevier Ltd.

Vincent Riambau et al., "Application of the Bolton Relay Device for Thoracic Endografting In or Near the Aortic Arch", Aorta, Feb. 2015, pp. 16-24, vol. 3 Issue 1, Science International Corp., http://aorta.scienceinternational.org.

R. Spear et al., "Editor's Choice e Subsequent Results for Arch Aneurysm Repair with Inner Branched Endografts", Arch Aneurysm Endovascular Repair, Dec. 8, 2015, pp. 380-385., European Society for Vascular Surgery, Elsevier Ltd.

R. Spear et al., "Complex endovascular repair of postdissection arch and thoracoabdominal aneurysms", Society for Vascular Surgery, Journal of Vascular Surgery, Sep. 5, 2017, pp. 1-8, Elsevier Inc.

R. Spear et al., "Total Endovascular Treatment of Aortic Arch Disease Using an Arch Endograft With 3 Inner Branches", Journal of Endovascular Therapy, 2017, pp. 534-538, vol. 24(4), Sage Publications.

Zhong Gao Wang, "Single-Branch Endografl for Treating Stanford Type B Aortic Dissections With Entry Tears in Proximity to the Left Subclavian Artery", J Endovasc Ther, 2005, pp. 588-593, International Society of Endovascular Specialists.

U.S. Appl. No. 62/430,218, of Keith Perkins et al., titled "Modular Aortic Arch Prosthetic Assembly and Method of Use Thereof", filed Dec. 5, 2016.

U.S. Appl. No. 62/687,087, of Keith Perkins et al., titled "Modular Stent Device for Multiple Vessels", filed Jun. 19, 2018.

(56) References Cited

OTHER PUBLICATIONS

U.S. Appl. No. 15/830,221, of Keith Perkins et al., titled "Modular Aortic Arch Prosthetic Assembly and Method of Use Thereof", filed Dec. 4, 2017.
U.S. Appl. No. 16/367,889, of Keith Perkins et al., titled "Modular Stent Device for Multiple Vessels and Method", filed Dec. 4, 2017.
U.S. Appl. No. 16/367,906, of Keith Perkins et al., titled "Supra Aortic Access Modular Stent Assembly and Method", filed Mar. 28, 2019.
International Search Report, Application No. PCT/US2019/024676, dated Jun. 17, 2019, pp. 1-14.
U.S. Appl. No. 16/502,462, of Keith Perkins et al., titled "Single Multibranch Stent Device Assembly and Method", filed Jul. 3, 2019.
U.S. Appl. No. 16/554,813, of Keith Perkins et al., titled "Modular Multibranch Stent Assembly and Method", filed Aug. 29, 2019.
U.S. Appl. No. 16/585,722, of Keith Perkins et al., titled "Docking Graft for Placement of Parallel Distally Extending Grafts Assembly and Method", filed Sep. 27, 2019.
U.S. Appl. No. 16/585,768, of Keith Perkins et al., titled "Supra Aortic Access Trifurcated Modular Stent Assembly and Method", filed Sep. 27, 2019.
U.S. Appl. No. 16/527,769, of Keith Perkins et al., titled "Modular Multibranch Stent Assembly and Method", filed Jul. 31, 2019.
U.S. Appl. No. 16/554,803, of Ashish Dhawan et al., titled "Use of Multiple Charged Ionic Compounds Derived From Polyamines for Waste Water Clarification", filed Aug. 29, 2019.
PCT/US2020/023170, The International Search Report and the Written Opinion of the International Searching Authority, dated Jun. 30, 2020, 12 pages.
PCT/US2020/023176, The International Search Report and the Written Opinion of the International Searching Authority, dated Jun. 19, 2020, 15 pages.

FEMORAL AORTIC ACCESS MODULAR STENT ASSEMBLY AND METHOD

RELATED APPLICATIONS

This application is a continuation of U.S. patent application Ser. No. 16/367,922, entitled "FEMORAL AORTIC ACCESS MODULAR STENT ASSEMBLY AND METHOD", filed Mar. 28, 2019, and issued as U.S. Pat. No. 11,083,605 on Aug. 10, 2021, which is incorporated herein by reference for all purposes.

BACKGROUND

Field

The present technology is generally related to an intra-vascular device and method. More particularly, the present application relates to a device for treatment of intra-vascular diseases.

Description of Related Art

Aneurysms, dissections, penetrating ulcers, intramural hematomas and/or transections may occur in blood vessels, and most typically occur in the aorta and peripheral arteries. The diseased region of the aorta may extend into areas having vessel bifurcations or segments of the aorta from which smaller "branch" arteries extend.

The diseased region of the aorta can be bypassed by use of a stent-graft placed inside the vessel spanning the diseased portion of the aorta, to seal off the diseased portion from further exposure to blood flowing through the aorta.

The use of stent-grafts to internally bypass the diseased portion of the aorta is not without challenges. In particular, care must be taken so that critical branch arteries are not covered or occluded by the stent-graft yet the stent-graft must seal against the aorta wall and provide a flow conduit for blood to flow past the diseased portion.

SUMMARY

The techniques of this disclosure generally relate to a first modular stent device that is deployed into the ascending aorta via femoral access. The first modular stent device is a base or anchor component to which additional modular stent devices can be attached to exclude diseased areas of the aorta while at the same time allowing perfusion of the brachiocephalic artery, the left common carotid artery, and/or the left subclavian artery.

In one aspect, the present disclosure provides an assembly including a first modular stent device. The first modular stent device includes a main body configured to be deployed in the ascending aorta, a bypass gate configured to be deployed in the aorta, and an artery leg configured to perfuse the brachiocephalic artery. The artery leg is shorter than the bypass gate. A second modular stent device includes a main body configured to be coupled to the bypass gate of the first modular stent device.

In another aspect, the present disclosure provides an assembly including a first modular stent device. The first modular stent device includes a main body, a bypass gate, and an artery leg. The artery leg is shorter than the bypass gate. The main body has a first longitudinal axis, the bypass gate has a second longitudinal axis, and the artery leg has a third longitudinal axis, and the first, second, and third longitudinal axes are parallel with one another when the first modular stent device is in a relaxed configuration. The assembly further comprises a stent-graft prosthesis configured to be coupled inside the bypass gate.

In yet another aspect, the present disclosure provides a method including deploying a first modular stent device. The deploying includes deploying a main body of the first modular stent device in the ascending aorta, deploying a bypass gate of the first modular stent device in the aorta, and deploying an artery leg of the first modular stent device to perfuse the brachiocephalic artery. The artery leg is shorter than the bypass gate. The method further includes deploying a main body of a second modular stent device in the bypass gate of the first modular stent device.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
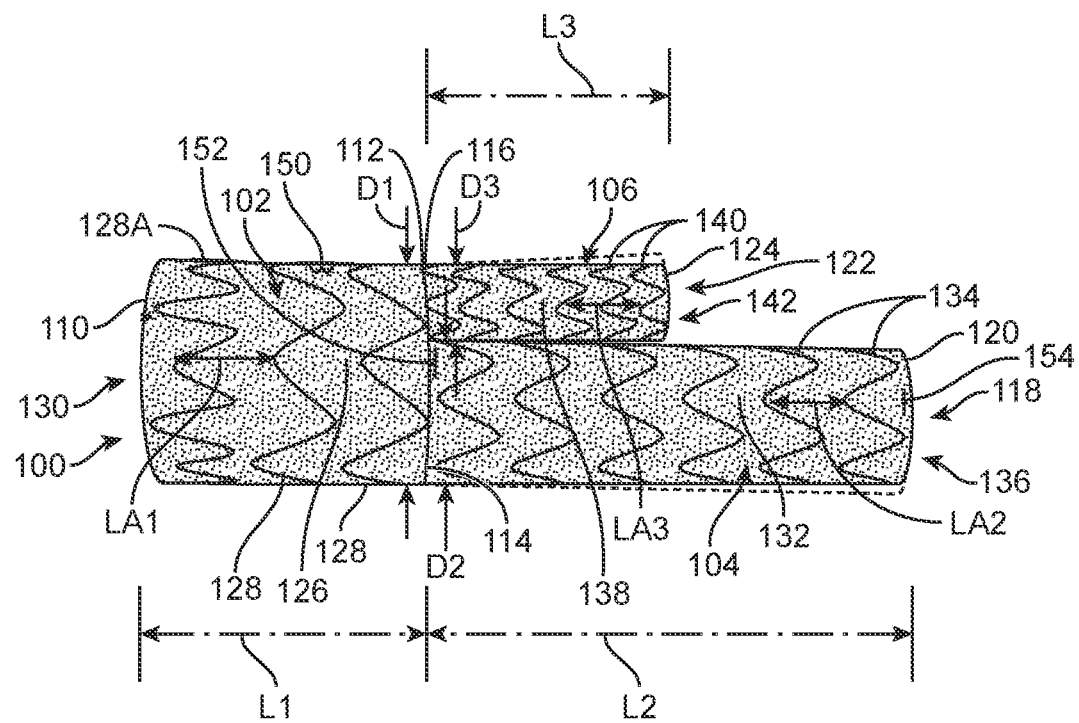
FIG. 1 is a side plan view of a modular stent device in accordance with one embodiment.
Figure 2:
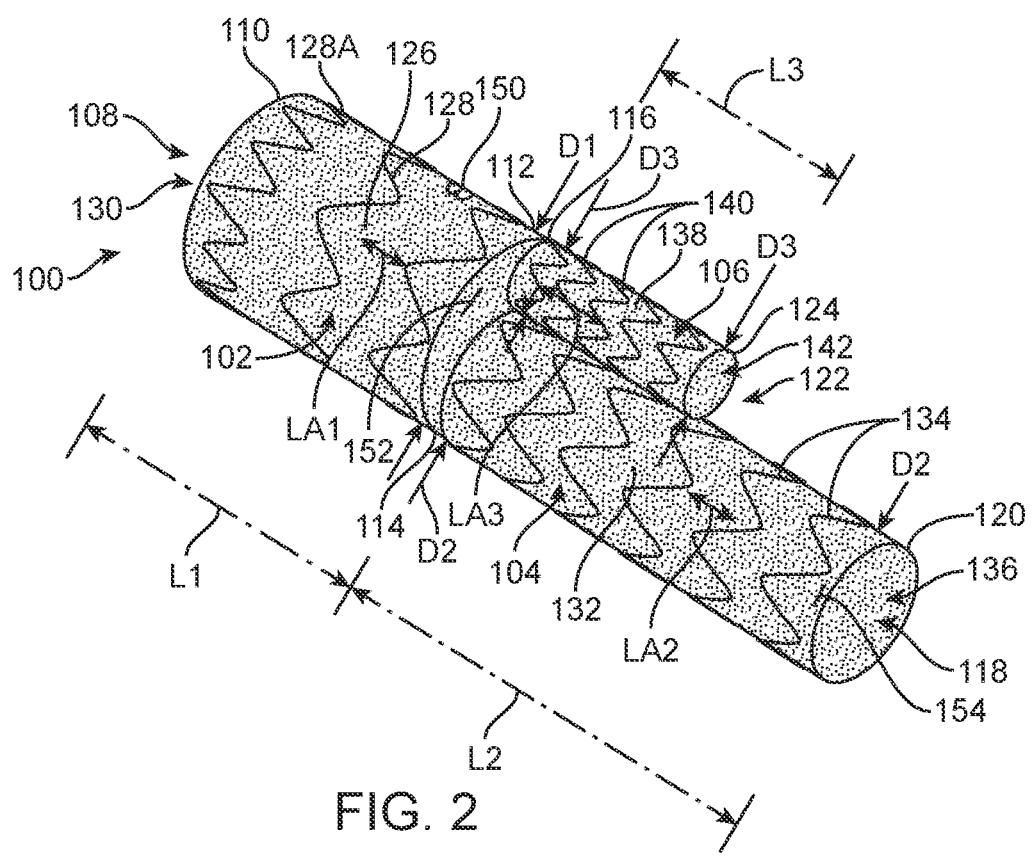
FIG. 2 is a perspective view of the modular stent device of FIG. 1 in accordance with one embodiment.

FIG. 1 is a side plan view of a modular stent device 100 in accordance with one embodiment. FIG. 2 is a perspective view of modular stent device 100 of FIG. 1 in accordance with one embodiment. Referring now to FIGS. 1 and 2 together, modular stent device 100, sometimes called a prosthesis or aortic arch prosthesis, includes a main body 102, a bypass gate 104 and an artery leg 106, sometimes called a brachiocephalic artery (BCA) leg/limb 106.

In accordance with this embodiment, main body 102 includes a main body proximal opening 108 at a proximal end 110 of main body 102. A distal end 112 of main body 102 is coupled to a proximal end 114 of bypass gate 104 and a proximal end 116 of artery leg 106.

Bypass gate 104 includes a bypass gate distal opening 118 at a distal end 120 of bypass gate 104. Artery leg 106 includes a leg distal opening 122 at a distal end 124 of artery leg 106. Openings 118, 122 are sometime called distal first and second openings 118, 122, respectively.

As used herein, the proximal end of a prosthesis such as modular stent device 100 is the end closest to the heart via the path of blood flow whereas the distal end is the end furthest away from the heart during deployment. In contrast and of note, the distal end of the catheter is usually identified to the end that is farthest from the operator/handle while the proximal end of the catheter is the end nearest the operator/handle.

For purposes of clarity of discussion, as used herein, the distal end of the catheter is the end that is farthest from the operator (the end furthest from the handle) while the distal end of modular stent device 100 is the end nearest the operator (the end nearest the handle), i.e., the distal end of the catheter and the proximal end of modular stent device 100 are the ends furthest from the handle while the proximal end of the catheter and the distal end of modular stent device 100 are the ends nearest the handle. However, those of skill in the art will understand that depending upon the access location, modular stent device 100 and the delivery system descriptions may be consistent or opposite in actual usage.

Main body 102 includes graft material 126 and one or more circumferential stents 128 coupled to graft material 126. Graft material 126 may be any suitable graft material, for example and not limited to, woven polyester, DACRON® material, expanded polytetrafluoroethylene, polyurethane, silicone, electro spun materials, or other suitable materials.

Circumferential stents 128 may be coupled to graft material 126 using stitching or other means. In the embodiment shown in FIGS. 1 and 2, circumferential stents 128 are coupled to an outside surface of graft material 126. However, circumferential stents 128 may alternatively be coupled to an inside surface of graft material 126.

Although shown with a particular number of circumferential stents 128, in light of this disclosure, those of skill in the art will understand that main body 102 may include a greater or smaller number of stents 128, e.g., depending upon the desired length of main body 102 and/or the intended application thereof.

Circumferential stents 128 may be any stent material or configuration. As shown, circumferential stents 128, e.g., self-expanding members, are preferably made from a shape memory material, such as nickel-titanium alloy (nitinol), and are formed into a zig-zag configuration. The configuration of circumferential stents 128 is merely exemplary, and circumferential stents 128 may have any suitable configuration, including but not limiting to a continuous or non-continuous helical configuration. In another embodiment, circumferential stents 128 are balloon expandable stents.

The circumferential stent 128A of the circumferential stents 128 which is disposed at proximal end 110 is referred to herein as the proximal-most stent 128A. In the embodiment of FIGS. 1 and 2, proximal-most stent 128A extends only to the edge of graft material 126 in a closed-web configuration as shown. However, in another embodiment, proximal-most stent 128A extends proximally past the edge of graft material 126 in an open-web or uncovered configuration.

Further, main body 102 includes a longitudinal axis LA1. A lumen 130 is defined by graft material 126, and generally by main body 102. Lumen 130 extends generally parallel to longitudinal axis LA1 and between proximal opening 108 and distal end 112 of main body 102. Graft material 126 is cylindrical having a substantially uniform diameter in this embodiment. However, in other embodiments, graft material 126 varies in diameter.

Bypass gate 104 includes graft material 132 and one or more circumferential stents 134 coupled to graft material 132. Graft material 132 may be any suitable graft material, for example and not limited to, woven polyester, DACRON® material, expanded polytetrafluoroethylene, polyurethane, silicone, electro spun materials, or other suitable materials.

Circumferential stents 134 may be coupled to graft material 132 using stitching or other means. In the embodiment shown in FIGS. 1 and 2, circumferential stents 134 are coupled to an outside surface of graft material 132. However, circumferential stents 134 may alternatively be coupled to an inside surface of graft material 132.

Although shown with a particular number of circumferential stents 134, in light of this disclosure, those of skill in the art will understand that bypass gate 104 may include a greater or smaller number of stents 134, e.g., depending upon the desired length of bypass gate 104 and/or the intended application thereof.

Circumferential stents 134 may be any stent material or configuration. As shown, circumferential stents 110, e.g., self-expanding members, are preferably made from a shape memory material, such as nickel-titanium alloy (nitinol), and are formed into a zig-zag configuration. The configuration of circumferential stents 134 is merely exemplary, and circumferential stents 134 may have any suitable configuration, including but not limiting to a continuous or non-continuous helical configuration. In another embodiment, circumferential stents 134 are balloon expandable stents.

Further, bypass gate 104 includes a longitudinal axis LA2. A lumen 136 is defined by graft material 132, and generally by bypass gate 104. Lumen 136 extends generally parallel to longitudinal axis LA2 and between proximal end 114 and distal opening 118 of bypass gate 104. Graft material 132 is cylindrical having a substantially uniform diameter in this embodiment. However, in other embodiments, graft material 132 varies in diameter.

Artery leg 106 includes graft material 138 and one or more circumferential stents 140 coupled to graft material 138. Graft material 138 may be any suitable graft material, for example and not limited to, woven polyester, DACRON® material, expanded polytetrafluoroethylene, polyurethane, silicone, electro spun materials, or other suitable materials.

Circumferential stents 140 may be coupled to graft material 138 using stitching or other means. In the embodiment shown in FIGS. 1 and 2, circumferential stents 140 are coupled to an outside surface of graft material 138. However, circumferential stents 140 may alternatively be coupled to an inside surface of graft material 138.

Although shown with a particular number of circumferential stents 140, in light of this disclosure, those of skill in the art will understand that artery leg 106 may include a greater or smaller number of stents 140, e.g., depending upon the desired length of artery leg 106 and/or the intended application thereof.

Circumferential stents 140 may be any stent material or configuration. As shown, circumferential stents 140, e.g., self-expanding members, are preferably made from a shape memory material, such as nickel-titanium alloy (nitinol), and are formed into a zig-zag configuration. The configuration of circumferential stents 140 is merely exemplary, and circumferential stents 140 may have any suitable configuration, including but not limiting to a continuous or non-continuous helical configuration. In another embodiment, circumferential stents 140 are balloon expandable stents.

Further, artery leg 106 includes longitudinal axis LA3. A lumen 142 is defined by graft material 138, and generally by artery leg 106. Lumen 142 extends generally parallel to longitudinal axis LA3 and between proximal end 116 and distal opening 122 of artery leg 106. Graft material 138 is cylindrical having a substantially uniform diameter in this embodiment. However, in other embodiments, graft material 138 varies in diameter.

Generally, main body 102 is bifurcated at distal end 112 into bypass gate 104 and artery leg 106. More particularly, lumen 130 of main body 102 is bifurcated into lumen 136 of bypass gate 104 and lumen 142 of artery leg 106. In one embodiment, graft materials 126, 132, 138 may be the same graft material, e.g., may be a single piece of graft material cut and sewn. However, in other embodiments, one or more of graft materials 126, 132, 138 may be different that the others of graft materials 126, 132, 138, e.g., different graft materials are cut and sewn together. In the relaxed configuration (unstressed) of modular stent device 100 as illustrated in FIGS. 1 and 2, longitudinal axes LA1, LA2, and LA3 are parallel with one another such that bypass gate 104 and artery leg 106 extend distally from main body 102.

Main body 102 has first diameter D1, bypass gate 104 has second diameter D2, and artery leg 106 has third diameter D3. In accordance with this embodiment, first diameter D1 is greater than second diameter D2. Further, second diameter D2 is greater than third diameter D3. In accordance with this embodiment, first diameter D1 is greater than second diameter D2 combined with third diameter D3 (D1>D2+D3) such that bypass gate 104 and artery leg 106 are located within an imaginary cylinder defined by graft material 126 of main body 102 extended in the distal direction. The parallel design mimics anatomical blood vessel bifurcations to limit flow disruptions.

In one embodiment, first diameter D1 is greater than second diameter D2 combined with third diameter D3 (D1>D2+D3) at distal end 112 and proximal ends 114, 116, sometimes called the transition region. However, main body 102, bypass gate 104 and/or artery leg 106, flare or taper away from the transition region in accordance with one embodiment, so D1>D2+D3 at the transition region but is not necessarily correct in regions away from the transition region. Flaring is indicated by the dashed lines in FIG. 1.

Stated another way, the transition region from main body 102 to artery leg 106 and bypass gate 104 does not exceed first diameter D1 of main body 102. This insures artery leg 106 and bypass gate 104 don't crush each other or negatively impact flow in any way. By avoiding having artery leg 106 and bypass gate 104 extend out wider than main body 102, a good seal of stents 128 of main body 102 against the aorta is insured and type I endoleaks are minimized or avoided.

In accordance with one embodiment, the transition region between main body 102 and artery leg 106 and bypass gate 104 is fully supported by one or more supporting stents, e.g., stents 128, 134, 140, to prevent kinking in angled anatomy. Absent the supporting stents, modular stent device 100 may be predispose to kinking in type III arches or gothic arches.

Main body 102 has a first length L1 in a direction parallel to the longitudinal axis LA1, bypass gate 104 has a second length L2 in a direction parallel to the longitudinal axis LA2, and artery leg 106 has a third length L3 in a direction parallel to the longitudinal axis LA3. In accordance with this embodiment, third length L3 is less than second length L2 such that distal opening 122 of artery leg 106 is proximal to distal opening 118 of bypass gate 104. Generally, artery leg 106 is shorter than bypass gate 104.

In one embodiment, first diameter D1 ranges from 26 mm to 54 mm. In another embodiment, first diameter D1 is smaller for a second device to treat the left common carotid or left subclavian artery and first diameter D1 is as small as 22 mm for transections. In one particular embodiment, first diameter D1 is in the range of 20 mm to 60 mm.

In one embodiment, second diameter D2 is any one of a number of values to accommodate a minimum diameter of artery leg 106 and the various possible diameters D1 of main body 102. In one embodiment, second diameter D2 of bypass gate 104 is maximized by subtracting the third diameter D3 of artery leg 106 from first diameter D1 of main body 102. For the brachiocephalic artery, also known as the innominate artery, the minimum diameter of artery leg 106 is suitably around 10 mm to 14 mm. Accordingly, when first diameter D1 is 20 mm, second diameter D2 of bypass gate 104 is 10 mm. However, second diameter D2 is as large as 50 mm in another embodiment. Suitably, second diameter D2 is in the approximate range of 10 mm to 46 mm.

Third diameter D3 is the diameter for the innominate artery, the left subclavian, and/or the left common carotid in one embodiment. The innominate artery ranges in size from approximately 10 mm up to 24 mm. The left subclavian artery size range is closer to 8 mm to 14 mm and the left common carotid artery is in the 6 mm to 10 mm range. Accordingly, third diameter D3 is suitably in the approximate range of 6 mm to 24 mm and in one particular embodiment is in the approximate range of 5 mm to 22 mm.

In one embodiment, landing is targeted in the middle of the ascending aorta. The distance between the sinotubular junction STJ and innominate artery ranges in size from 4-8 cm so first length L1 is suitably in the range of around 4 cm to 8 cm. However, to extend coverage all the way to the sinotubular junction STJ, in one embodiment, first length L1 can vary. Suitably, first length L1 is in the approximate range of 10 mm to 160 mm. Alternatively, a proximal cuff is used as discussed further below.

Second length L2 is suitably sufficient for providing adequate overlap in an environment with significant respiratory and cardiac induced motion. It is also suitable to space bypass gate 104 so that bypass gate 104 does not inadvertently open inside of a target branch. In one embodiment, second length L2 is suitably in the approximate range of 10 mm to 240 mm and in one particular embodiment is in the range of 20 mm to 70 mm. In one embodiment, the minimum overlap is shortened by providing some mechanism for anchoring of the device.

Third length L3 is less than second length L2. In one embodiment, artery leg 106 is extended with additional devices.

Although fixed diameters D1, D2, and D3 are illustrated and discussed, in one embodiment, main body 102, bypass gate 104 and/or artery leg 106 are non-uniform in diameter. For example, main body 102 flares or tapers at proximal end 110. Similarly, bypass gate 104 and/or artery leg 106 flare or taper at distal ends 120, 124, respectively. For example, bypass gate 104 and/or artery leg 106 flare or taper at distal ends 120, 124 to enhance sealing.

Artery leg 106 is configured to exert a higher radial force than the radial force of bypass gate 104. As used herein, "radial force" includes both a radial force exerted during expansion/deployment as well as a chronic radial force continuously exerted after implantation such that a scaffold has a predetermined compliance or resistance as the surrounding native anatomy, e.g., the aorta, expands and contracts during the cardiac cycle. The radial force of bypass gate 104 is configured to be lower than that of artery leg 106 in order to avoid collapse of artery leg 106 when bypass gate 104 is deployed against and adjacent thereof and thus maintain perfusion of the brachiocephalic artery as discussed further below.

To configure bypass gate 104 and artery leg 106 with differing relative radial forces, circumferential stents 140 of artery leg 106 be constructed with relatively thicker and/or shorter segments of material than circumferential stents 134 of bypass gate 104. Shorter and/or thicker circumferential stents 140 have less flexibility but greater radial force to ensure that circumferential stents 134 of bypass gate 104 do not collapse lumen 142 of artery leg 106. Other variations or modification of circumferential stents 134, 140 may be used to achieve relative radial forces in other embodiments.

Modular stent device 100 includes radiopaque markers 150, 152, 154. In accordance with this embodiment, radiopaque marker 150 is shaped as a FIG. 8 marker, i.e., in the shape of the number 8. Radiopaque marker 150 is sewn into graft material 126 in line with artery leg 106. Under fluoroscopy, radiopaque marker 150 is rotated so that it is seen on the edge on the outer curvature of the aortic arch in one embodiment so that artery leg 106 is accurately and reproducibly deployed on the outer curve of the aorta.

Radiopaque maker 152 is sewn in the transition region where main body 102 meets bypass gate 104 and artery leg 106 to indicate the desired extent of overlap. Radiopaque marker 154, e.g., a coil marker, is sewn into bypass gate 104 to aid in cannulation of bypass gate 104.

Figure 3:
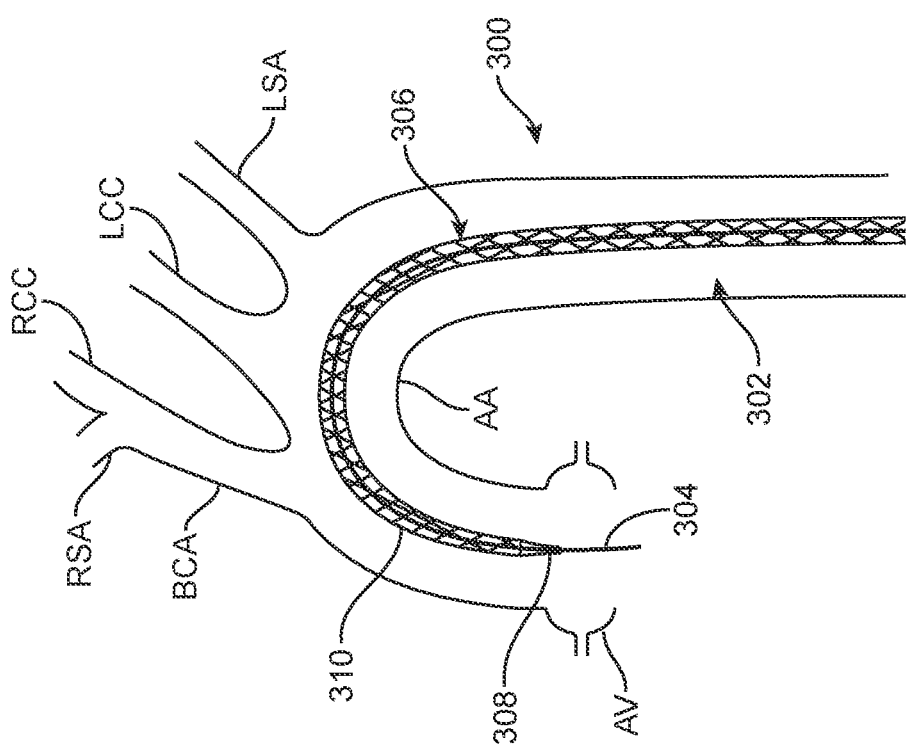
FIG. 3 is a cross-sectional view of a vessel assembly including the modular stent device of FIGS. 1 and 2 during deployment in accordance with one embodiment.

FIG. 3 is a cross-sectional view of a vessel assembly 300 including modular stent device 100 of FIGS. 1 and 2 during deployment in accordance with one embodiment.

Referring to FIGS. 1, 2 and 3 together, the thoracic aorta 302 has numerous arterial branches. The arch AA of the aorta 302 has three major branches extending therefrom, all of which usually arise from the convex upper surface of the arch AA. The brachiocephalic artery BCA originates anterior to the trachea. The brachiocephalic artery BCA divides into two branches, the right subclavian artery RSA (which supplies blood to the right arm) and the right common carotid artery RCC (which supplies blood to the right side of the head and neck). The left common carotid artery LCC artery arises from the arch AA of the aorta 302 just to the left of the origin of the brachiocephalic artery BCA. The left common carotid artery LCC supplies blood to the left side of the head and neck. The third branch arising from the aortic arch AA, the left subclavian artery LSA, originates behind and just to the left of the origin of the left common carotid artery LCC and supplies blood to the left arm.

However, a significant proportion of the population has only two great branch vessels coming off the aortic arch AA while others have four great branch vessels coming of the aortic arch AA. Accordingly, although a particular anatomical geometry of the aortic arch AA is illustrated and discussed, in light of this disclosure, those of skill in the art will understand that the geometry of the aortic arch AA has anatomical variations and that the various structures as disclosed herein would be modified accordingly.

Aneurysms, dissections, penetrating ulcers, intramural hematomas and/or transections, generally referred to as a diseased region of the aorta 302, may occur in the aorta arch AA and the peripheral arteries BCA, LCC, LSA. For example, thoracic aortic aneurysms include aneurysms present in the ascending thoracic aorta, the aortic arch AA, and one or more of the branch arteries BCA, LCC, LSA that emanate therefrom. Thoracic aortic aneurysms also include aneurysms present in the descending thoracic aorta and branch arteries that emanate therefrom. Accordingly, the aorta 302 as illustrated in FIG. 3 has a diseased region similar to any one of those discussed above which will be bypassed and excluded using modular stent device 100 as discussed below.

As illustrated in FIG. 3, a guide wire 304 is introduced via femoral access. In one particular embodiment, guidewire 304 is inserted into the femoral artery and routed up through the abdominal aorta, and into the thoracic aorta.

A delivery system 306 including modular stent device 100 is introduced via femoral access and is advanced into the ascending aorta 302 over guidewire 304. Delivery system 306 is positioned at the desired location such that the position of modular stent device 100 is in the ascending aorta near the aortic valve AV.

In accordance with this embodiment, delivery system 306 includes a tip capture mechanism 308 and a delivery sheath 310. Delivery sheath 310 maintains modular stent device 100 in a collapsed configuration during delivery to the desired location within the aorta 302. Tip capture mechanism 308 captures proximal end 110 of main body 102, e.g., proximal circumferential stent 128A, and keeps proximal end 110 in a collapsed configuration until released. Tip capture mechanism 308 controls proximal deployment accuracy in a highly mobile environment with large amounts of fluid flow, e.g., in the ascending aorta.

Figure 4:
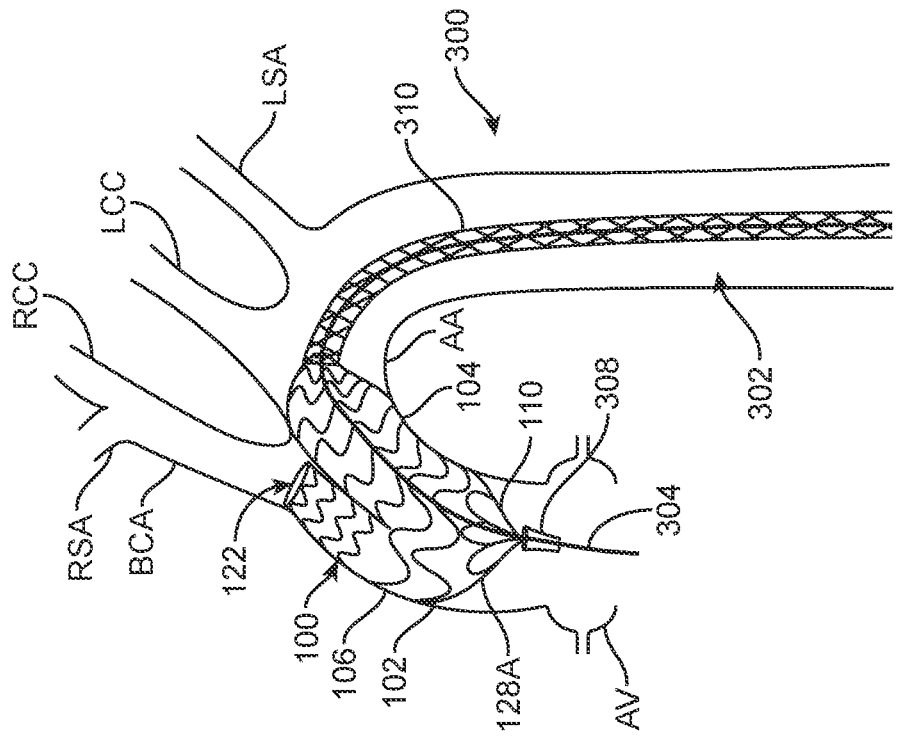
FIG. 4 is a cross-sectional view of the vessel assembly of FIG. 3 at a later stage during deployment of the modular stent device in accordance with one embodiment.

FIG. 4 is a cross-sectional view of vessel assembly 300 of FIG. 3 at a later stage during deployment of modular stent device 100 in accordance with one embodiment. Referring now to FIGS. 3 and 4 together, delivery sheath 310 is withdrawn to expose main body 102, artery leg 106, and the proximal most portion of bypass gate 104. This deploys main body 102 and artery leg 106. Artery leg 106 is opened thus insuring perfusion to distal territories, e.g., including the brachiocephalic artery BCA. In accordance with this embodiment, distal opening 122 of artery branch 106 is proximal to the brachiocephalic artery BCA allowing easy cannulation thereof as discussed below.

To allow adjustment of the position of modular stent device 100, proximal end 110 of main body 102 remains captured within tip capture mechanism 308 and the distal portion of bypass gate 104 remains collapsed and captured within delivery sheath 310. Modular stent device 100 is moved, e.g., proximally or distally and/or rotated, if necessary, until positioned at the desired location. The closed web tip capture system of tip capture mechanism 308 insures accurate deployment at the sinotubular junction STJ to maximize the proximal seal of modular stent device 100 in the aorta 302.

Figure 5:
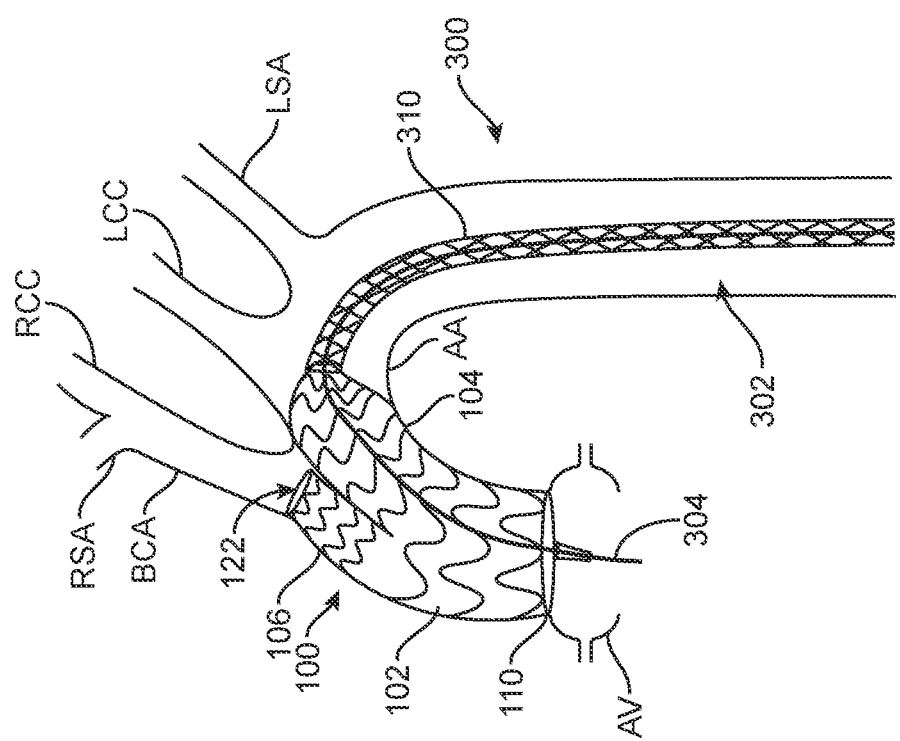
FIG. 5 is a cross-sectional view of the vessel assembly of FIG. 4 at a later stage during deployment of the modular stent device in accordance with one embodiment.

FIG. 5 is a cross-sectional view of vessel assembly 300 of FIG. 4 at a later stage during deployment of modular stent device 100 in accordance with one embodiment. Referring to FIGS. 4 and 5 together, proximal end 110 of main body 102 is released from tip capture mechanism 308 and thus expands into aorta 302. However, in another embodiment, proximal end 110 of main body 102 remains captured within tip capture mechanism 308 at this stage of deployment, for example, as illustrated in FIG. 6.

Figure 6:
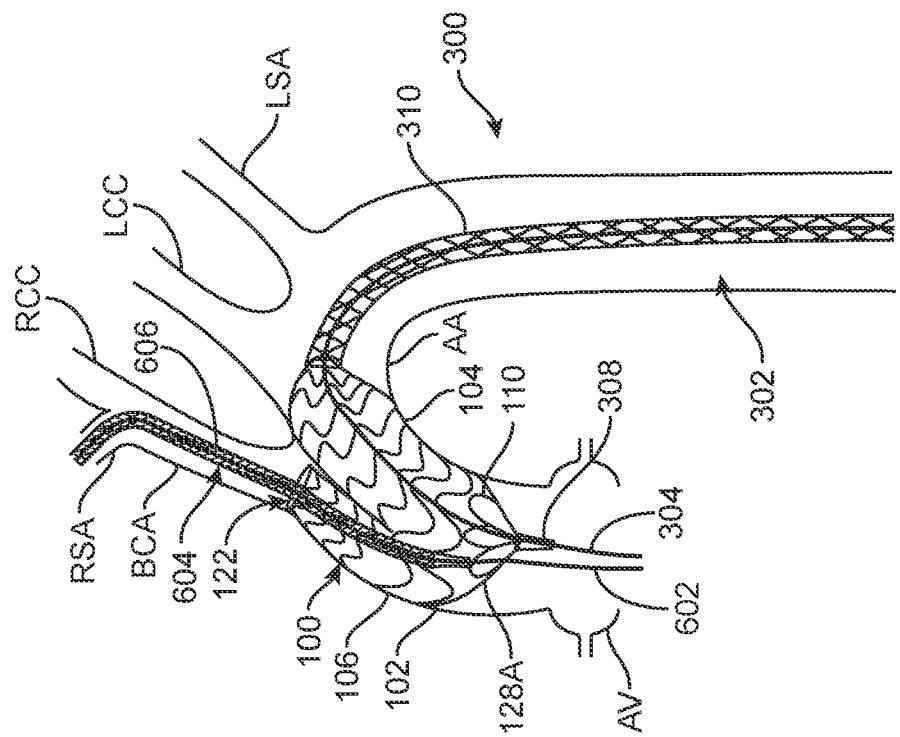
FIG. 6 is a cross-sectional view of the vessel assembly of FIG. 4 at a later stage during deployment of the modular stent device in accordance with another embodiment.

FIG. 6 is a cross-sectional view of vessel assembly 300 of FIG. 4 at a later stage during deployment of modular stent device 100 in accordance with another embodiment. Referring now to FIG. 6, proximal end 110 of main body 102 remains captured within tip capture mechanism 308 in accordance with this embodiment. Further, the distal portion of bypass gate 104 remains collapsed and captured within delivery sheath 310. This allows control of modular stent device 100, e.g., to allow modular stent device 100 to be held in place or to have the position thereof adjusted.

A second guidewire 602 is introduced via supra aortic access, e.g., through the right subclavian artery RSA, and advanced into the ascending aorta 302. More particularly, guidewire 602 is passed into distal opening 122 of artery leg 106, through artery leg 106, through main body 102 and out of proximal opening 108 of main body 102. A bridging stent graft delivery system 604 including a bridging stent graft is advanced via supra aortic access into artery leg 106 over guidewire 602.

Figure 7:
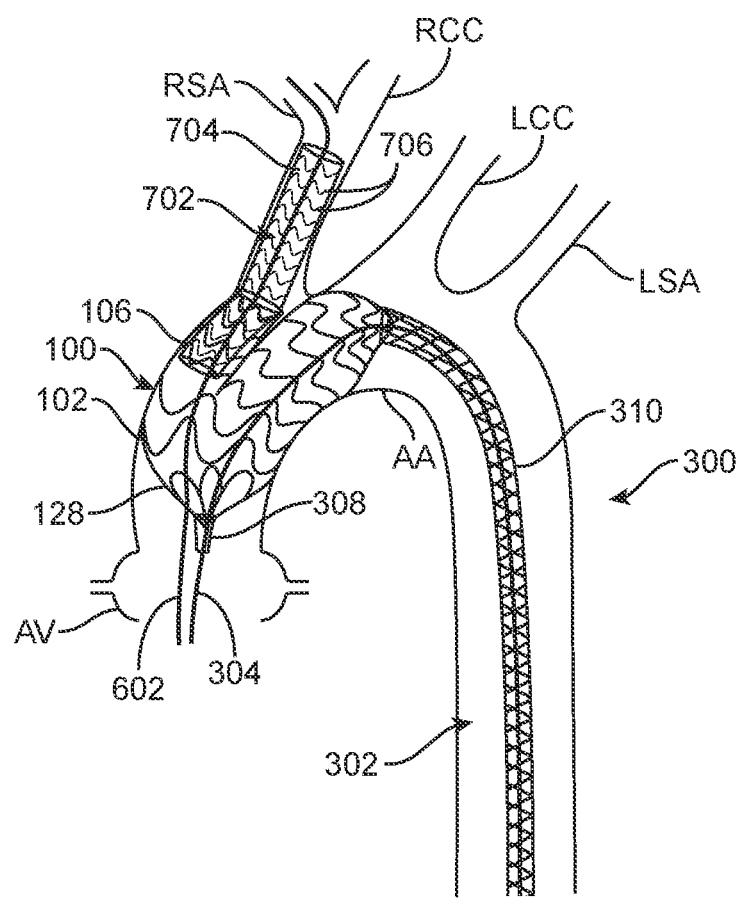
FIG. 7 is a cross-sectional view of the vessel assembly of FIG. 6 at a later stage during deployment of a bridging stent graft in accordance with one embodiment.

FIG. 7 is a cross-sectional view of vessel assembly 300 of FIG. 6 at a later stage during deployment of a bridging stent graft 702, sometimes called a bridging stent, in accordance with one embodiment. Referring to FIGS. 6 and 7 together, a delivery sheath 606 (FIG. 6) of bridging stent graft delivery system 604 is completely withdrawn to expose the entirety of bridging stent graft 702. This deploys bridging stent graft 702 within artery leg 106 and the brachiocephalic artery BCA. More particularly, bridging stent graft 702 self-expands to be anchored within artery leg 106 and the brachiocephalic artery BCA.

Bridging stent graft 702 includes graft material 704 and one or more circumferential stents 706. Upon deployment of bridging stent graft 702, blood flow into artery leg 106 is bridged and passed into the brachiocephalic artery BCA through bridging stent graft 702.

Figure 8:
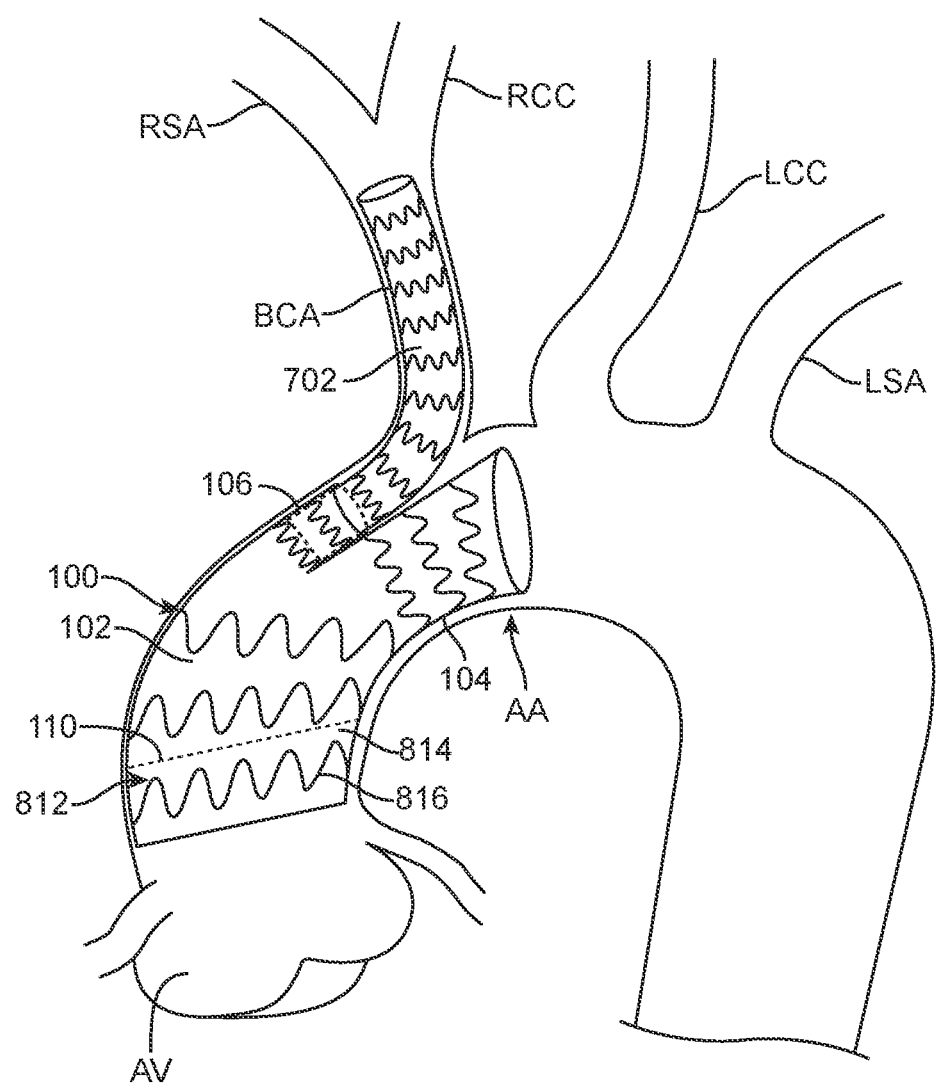
FIG. 8 is a cross-sectional view of the vessel assembly of FIG. 7 at a later stage during deployment of the modular stent device in accordance with one embodiment.

FIG. 8 is a cross-sectional view of vessel assembly 300 of FIG. 7 at a later stage during deployment of modular stent device 100 in accordance with one embodiment. Referring to FIGS. 7 and 8 together, delivery sheath 310 (FIG. 7) of delivery system 306 is completely withdrawn to expose the entirety of bypass gate 104. This deploys bypass gate 104 within the aorta 302. More particularly, bypass gate 104 self-expands to be anchored within the aorta 302.

As artery leg 106 has a greater radial force than bypass gate 104, artery leg 106 remains un-collapsed and opened. Accordingly, blood flow through artery leg 106 including bridging stent graft 702 and perfusion of the brachiocephalic artery BCA is insured. This avoids stroke, or other medical complications from occlusion of the brachiocephalic artery BCA.

Perfusion of the brachiocephalic artery BCA is immediate and dependable. More particularly, artery leg 106 is released and opened during the initial deployment of modular stent device 100 thus insuring perfusion of the brachiocephalic artery BCA.

If there is any collapse between artery leg 106 and bypass gate 104, the collapse is in bypass gate 104. However, bypass gate 104 has a sufficiently large diameter D2 such that any collapse of bypass gate 104 is partial and blood flow through bypass gate 104 and aorta 302 is maintained.

Further, as illustrated in FIG. 8, optionally, a proximal cuff 812 is coupled to main body 102 of modular stent device 100 and extend proximately therefrom. For example, proximal cuff 812 is deployed in the event that proximal end 110 of main body 102 is deployed distally from the aortic valve AV to extend between the desired deployment location and proximal end 110 of main body 102. Proximal cuff 812 is optional and in one embodiment is not deployed or used.

Proximal cuff 812 includes graft material 814 and one or more circumferential stents 816. Graft material 814 includes any one of the graft materials as discussed above in relation to graft materials 126, 132, 138. In addition, circumferential stents 816 are similar to or identical to anyone of circumferential stents 128, 134, 140 as discussed above.

Figure 9:
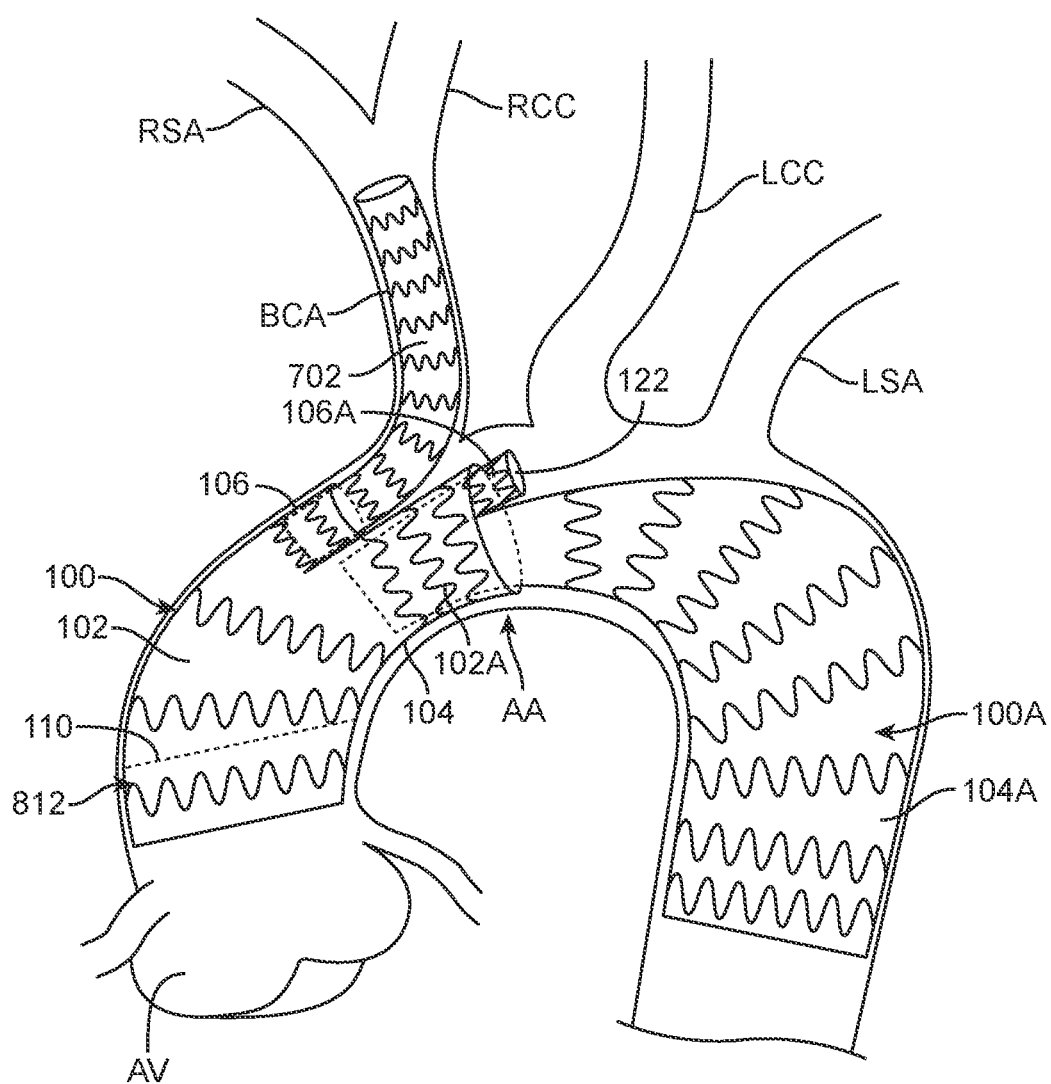
FIG. 9 is a cross-sectional view of the vessel assembly of FIG. 8 at a later stage during deployment of a second modular stent device in accordance with another embodiment.

FIG. 9 is a cross-sectional view of vessel assembly 300 of FIG. 8 at a later stage during deployment of a second modular stent device 100A in accordance with another embodiment. Second modular stent device 100A is the same or similar to modular stent device 100, the discussion of which is applicable to the second modular stent device 100A.

In accordance with this embodiment, second modular stent device 100A is deployed within bypass gate 104 of modular stent device 100 via femoral access in a manner similar to that discussed above regarding modular stent device 100.

More particularly, a main body 102A of second modular stent device 100A is located within bypass gate 104 of modular stent device 100, sometime called a first modular stent device 100. A bypass gate 104A of second modular stent device 100A is located within aorta 302 and arranged to point away and distally from first modular stent device 100. In accordance with this embodiment, distal opening 122 of an artery branch 106A of second modular stent device 100A is proximal to the left common carotid artery LCC and/or the left subclavian artery LSA allowing easy cannulation thereof as discussed below.

Figure 10:
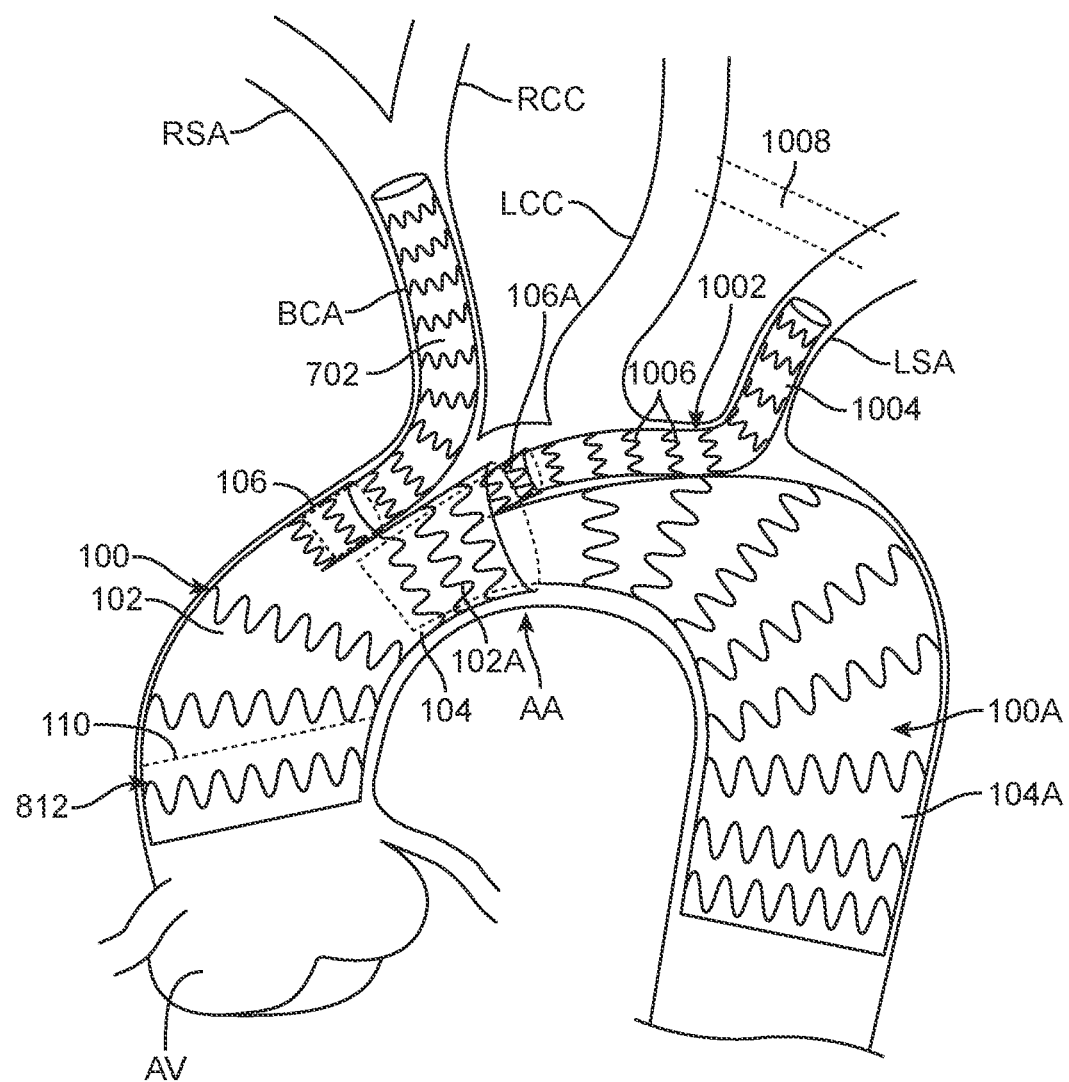
FIG. 10 is a cross-sectional view of the vessel assembly of FIG. 9 at a later stage during deployment of a bridging stent graft in accordance with one embodiment.

In accordance with this embodiment, blood flow enters second modular stent device 100A through main gate 102A, and exits through bypass gate 104A and artery leg 106A. Accordingly, blood flow through artery leg 106A and perfusion of the left common carotid artery LCC and/or the left subclavian artery LSA is insured. I FIG. 10 is a cross-sectional view of vessel assembly 300 of FIG. 9 at a later stage during deployment of a bridging stent graft 1002, sometimes called a bridging stent, in accordance with one embodiment. Referring to FIGS. 9 and 10 together, bridging stent graft 1002 is deployed within artery leg 106A and the left subclavian artery LSA. More particularly, bridging stent graft 1002 self-expands to be anchored within artery leg 106A and the left subclavian artery LSA. Bridging stent graft 1002 is deployed via supra aortic access through the left subclavian artery LSA in a manner similar to that discussed above regarding deployment of bridging stent graft 702.

Bridging stent graft 1002 includes graft material 1004 and one or more circumferential stents 1006. Upon deployment of bridging stent graft 1002, blood flow into artery leg 106A is bridged and passed into the left subclavian artery LSA through bridging stent graft 1002. In this manner, any overlapped diseased regions of the aorta 302 are excluded.

In accordance with this embodiment, modular stent device 100A and/or bridging stent graft 1002 overlaps, excludes and thus occludes the left common carotid artery LCC. In accordance with this embodiment, a bypass 1008 provides perfusion to the left common carotid artery LCC. Illustratively, bypass 1008 provides perfusion of the left common carotid artery LCC from the left subclavian artery LSA.

Bypass 1008 is surgically inserted during the same procedure as deployment of modular stent devices 100, 100A, and bridging stent grafts 702, 1002. However, in another embodiment, bypass 1008 is surgically inserted prior to deployment of modular stent devices 100, 100A, and bridging stent grafts 702, 1002, e.g., to simplify the procedure.

Figure 11:
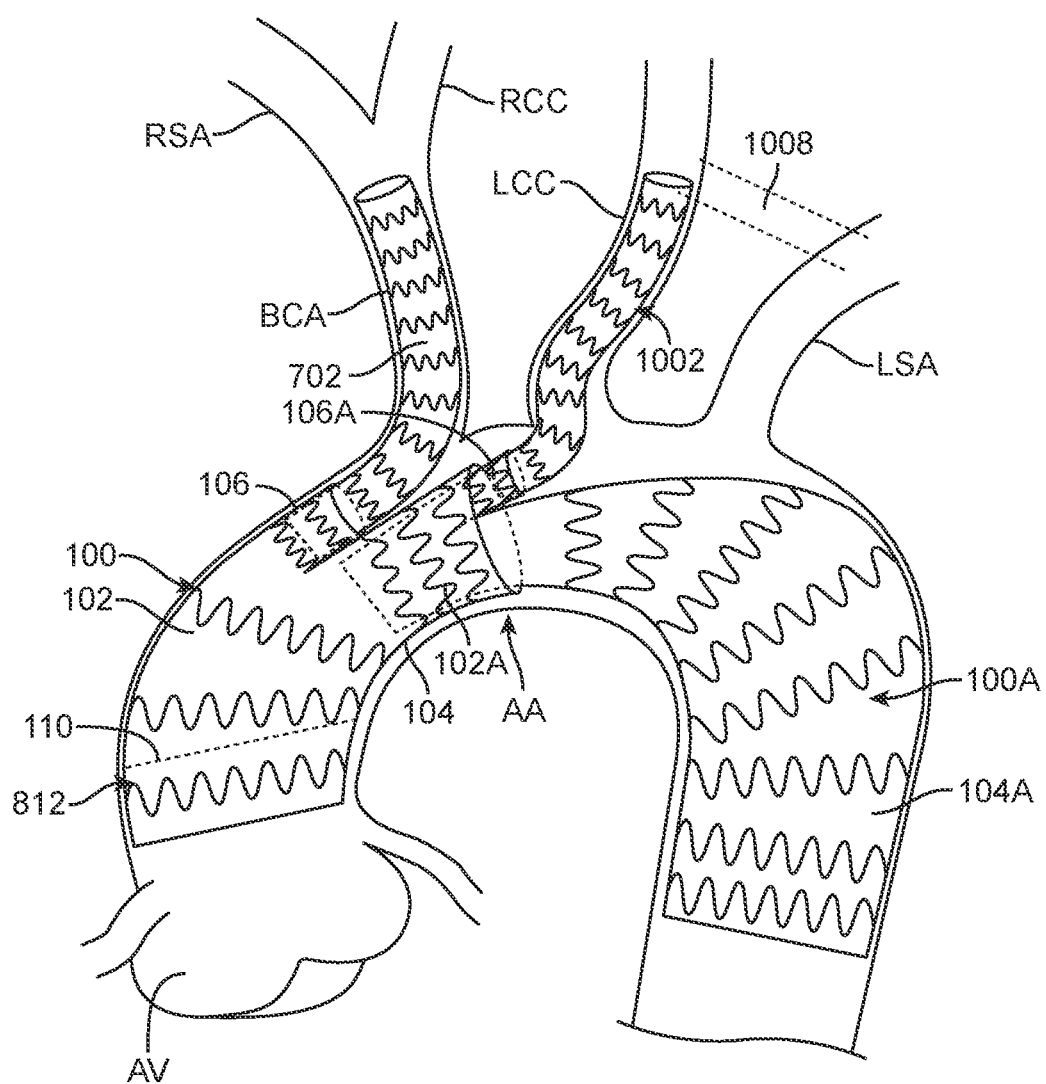
FIG. 11 is a cross-sectional view of the vessel assembly of FIG. 9 at a later stage during deployment of the bridging stent graft in accordance with another embodiment.

FIG. 11 is a cross-sectional view of vessel assembly 300 of FIG. 9 at a later stage during deployment of bridging stent graft 1002 in accordance with another embodiment. Vessel assembly 300 of FIG. 11 is similar to vessel assembly 300 of FIG. 10 and only the significant differences are discussed below.

Referring to FIGS. 9 and 11 together, bridging stent graft 1002 is deployed within artery leg 106A and the left common carotid artery LCC. More particularly, bridging stent graft 1002 self-expands to be anchored within artery leg 106A and the left common carotid artery LCC. Bridging stent graft 1002 is deployed via supra aortic access through the left common carotid artery LCC in a manner similar to that discussed above regarding deployment of bridging stent graft 702.

Upon deployment of bridging stent graft 1002, blood flow into artery leg 106A is bridged and passed into the left common carotid artery LCC through bridging stent graft 1002. In this manner, any overlapped diseased regions of the aorta 302 are excluded.

In accordance with this embodiment, modular stent device 100A and/or bridging stent graft 1002 overlaps, excludes and thus occludes the left subclavian artery LSA. In accordance with this embodiment, bypass 1008 provides perfusion to the left subclavian artery LSA. Illustratively, bypass 1008 provides perfusion of the left subclavian artery LSA from the left common carotid artery LCC.

Figure 12:
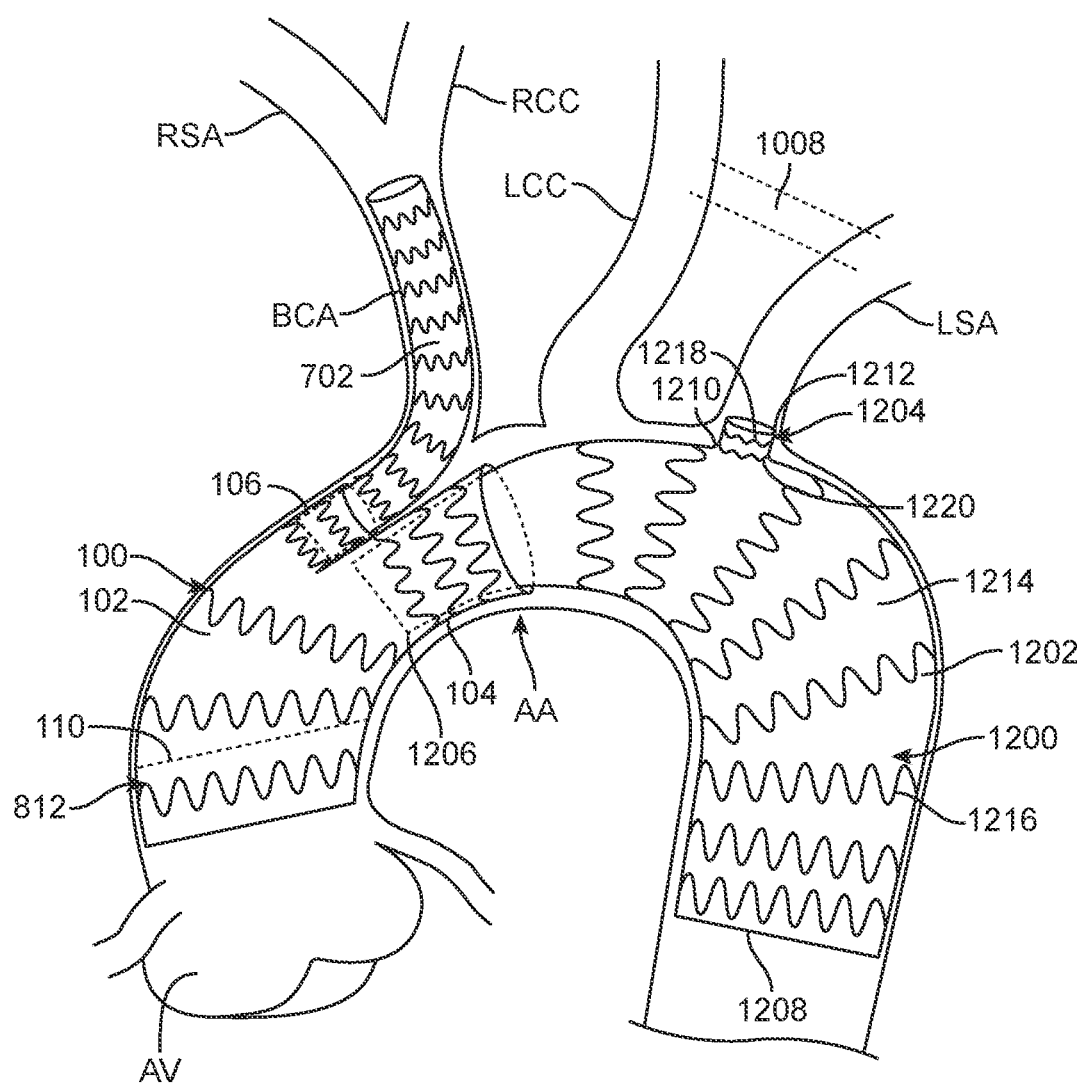
FIG. 12 is a cross-sectional view of the vessel assembly of FIG. 8 at a later stage during deployment of a distal aortic stent-graft prosthesis in accordance with another embodiment.

FIG. 12 is a cross-sectional view of vessel assembly 300 of FIG. 8 at a later stage during deployment of a distal aortic stent-graft prosthesis 1200, sometimes called a second modular stent device 1200, in accordance with another embodiment. Distal aortic stent-graft prosthesis 1200 includes a main body 1202 and a coupling 1204 extending radially from main body 1202.

Main body 1202 is generally cylindrically shaped but can vary in diameter in other embodiments. A proximal end 1206 of main body 1202 of distal aortic stent-graft prosthesis 1200 is deployed within bypass gate 104 of modular stent device 100 via femoral access. Main body 1202 extends distally from bypass gate 104 and a distal end 1208 of main body 1202 is deployed within the descending aorta 302. Generally, main body 1202 defines a lumen extending therethrough.

Main body 1202 is deployed such that coupling 1204 is aligned with the left subclavian artery LSA. Coupling 1204 corresponds with an opening in the main body 1202. Coupling 1204 is generally frustoconically shaped and includes a base 1210 and a top 1212. A circumference of base 1210 is greater than a circumference of top 1212. Coupling 1204 defines a lumen in fluid communication with the lumen of main body 1202.

Accordingly, blood flow exiting bypass gate 104 of modular stent device 100 enters proximal end 1206 of main body 1202. Blood flows through the lumen of main body 1202 and exits distal end 1208 and into the aorta 302.

Further, blood flow from the lumen of main body 1202 flows through coupling 1204 and into the left subclavian artery LSA. More particularly, blood flows enter into base 1210 of coupling 1204, through the lumen of coupling 1204, and exits top 1212 of coupling 1204 into the left subclavian artery LSA.

Main body 1202 includes graft material 1214 and one or more circumferential stents 1216. Graft material 1214 includes any one of the graft materials as discussed above in relation to graft materials 126, 132, 138. In addition, circumferential stents 1216 are similar to or identical to anyone of circumferential stents 128, 134, 140 as discussed above.

Coupling 1204 includes graft material 1218 and one or more circumferential stents 1220. Graft material 1218 includes any one of the graft materials as discussed above in relation to graft materials 126, 132, 138. In addition, circumferential stents 1216 are similar to or identical to anyone of circumferential stents 128, 134, 140 as discussed above.

Figure 13:
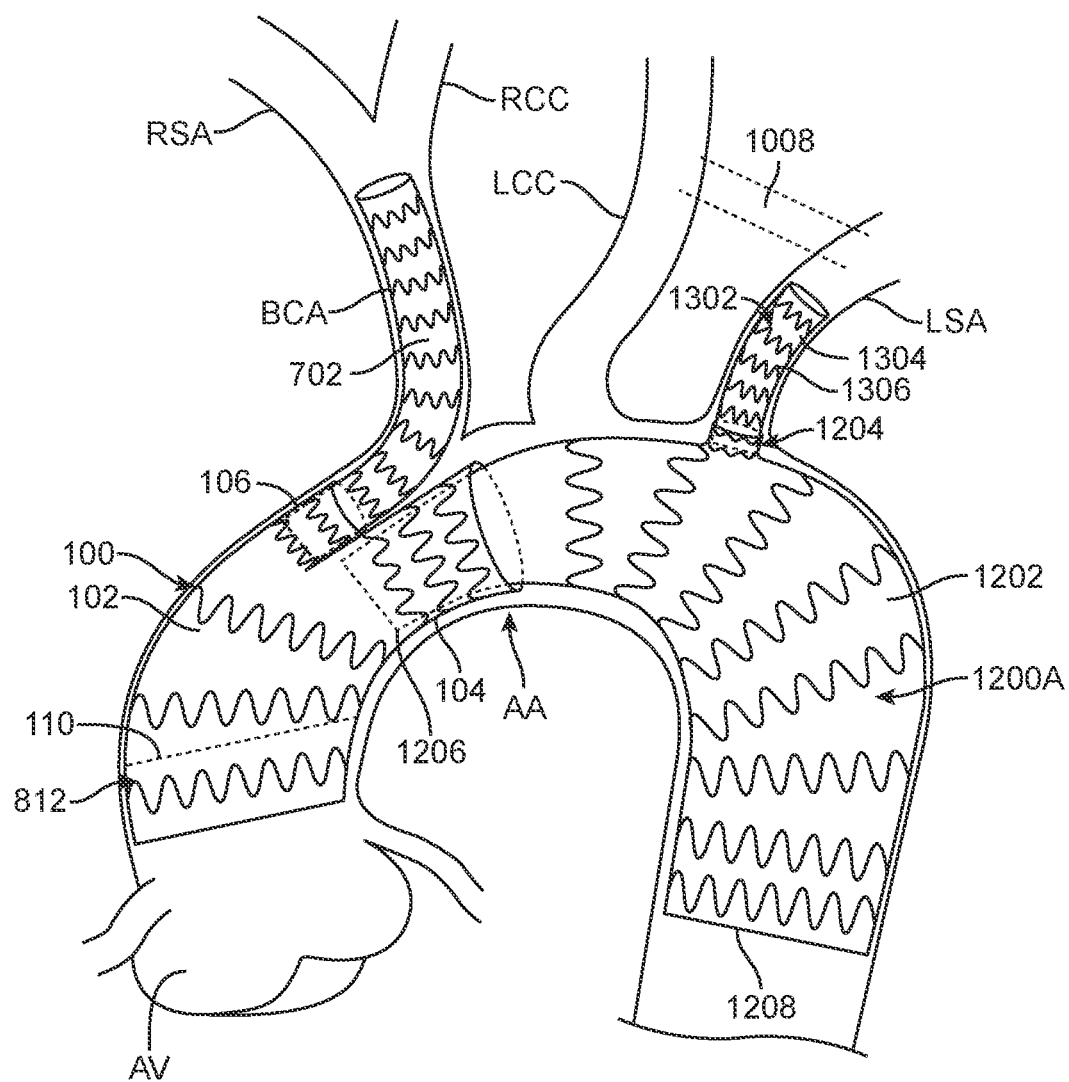
FIG. 13 is a cross-sectional view of the vessel assembly of FIG. 12 at a later stage during deployment of a bridging stent graft in accordance with one embodiment.

FIG. 13 is a cross-sectional view of vessel assembly 300 of FIG. 12 at a later stage during deployment of a bridging stent graft 1302 in accordance with one embodiment. Referring to FIGS. 12 and 13 together, bridging stent graft 1302 is deployed within coupling 1204 and within the left subclavian artery LSA. More particularly, bridging stent graft 1302 is anchored within coupling 1204 and the left subclavian artery LSA. Bridging stent graft 1302 is deployed via supra aortic access through the left subclavian artery LSA or alternatively through femoral access.

Bridging stent graft 1302 includes graft material 1304 and one or more circumferential stents 1306. Graft material 1304 includes any one of the graft materials as discussed above in relation to graft materials 126, 132, 138. In addition, circumferential stents 1306 are similar to or identical to anyone of circumferential stents 128, 134, 140 as discussed above.

Upon deployment of bridging stent graft 1302, blood flow into coupling 1204 is bridged and passed into the left subclavian artery LSA through bridging stent graft 1302.

In accordance with this embodiment, main body 1202 overlaps, excludes and thus occludes the left common carotid artery LCC. In accordance with this embodiment, bypass 1008 provides perfusion to the left common carotid artery LCC. Illustratively, bypass 1008 provides perfusion of the left common carotid artery LCC from the left subclavian artery LSA.

Figure 14:
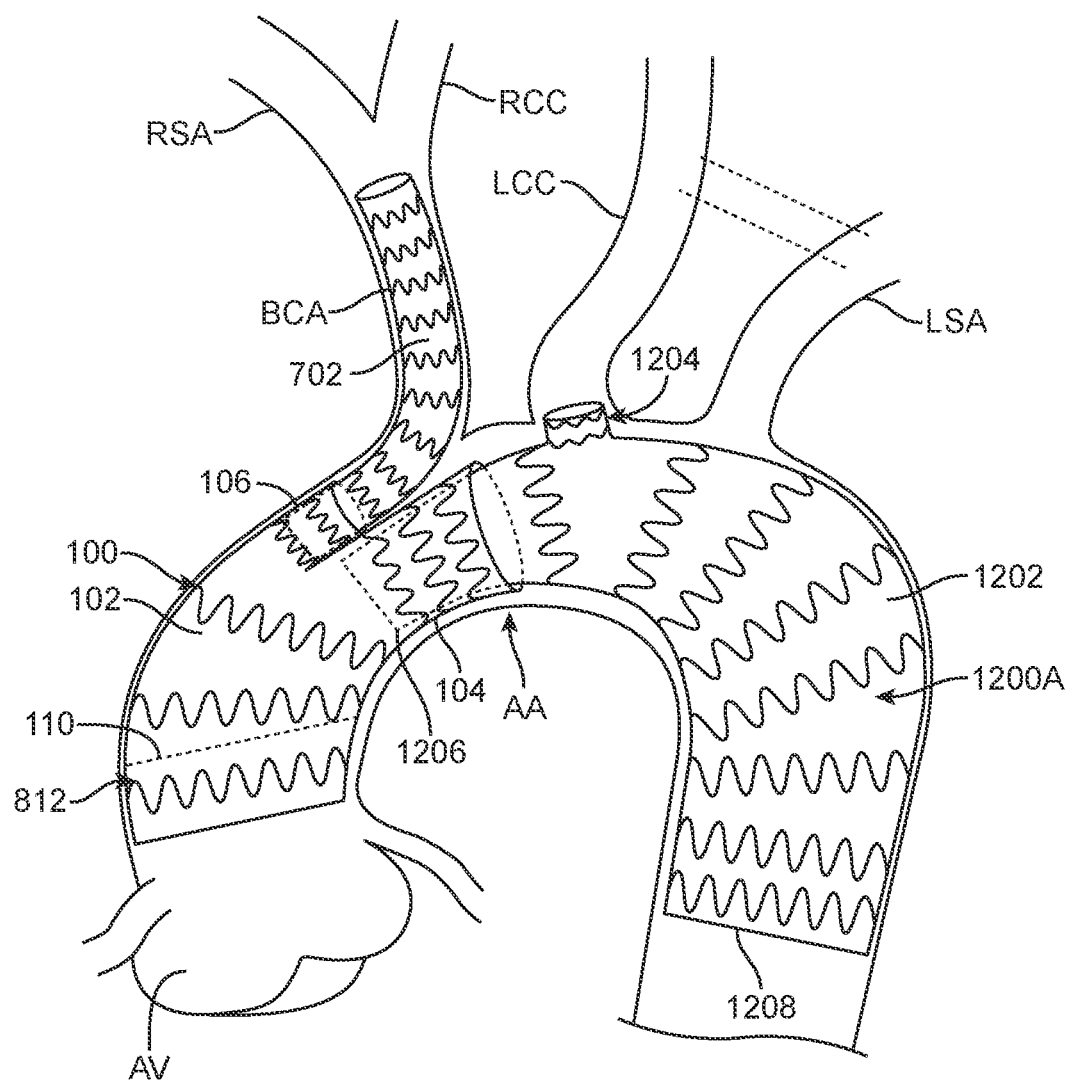
FIG. 14 is a cross-sectional view of the vessel assembly of FIG. 8 at a later stage during deployment of a distal aortic stent-graft prosthesis in accordance with another embodiment.
Figure 15:
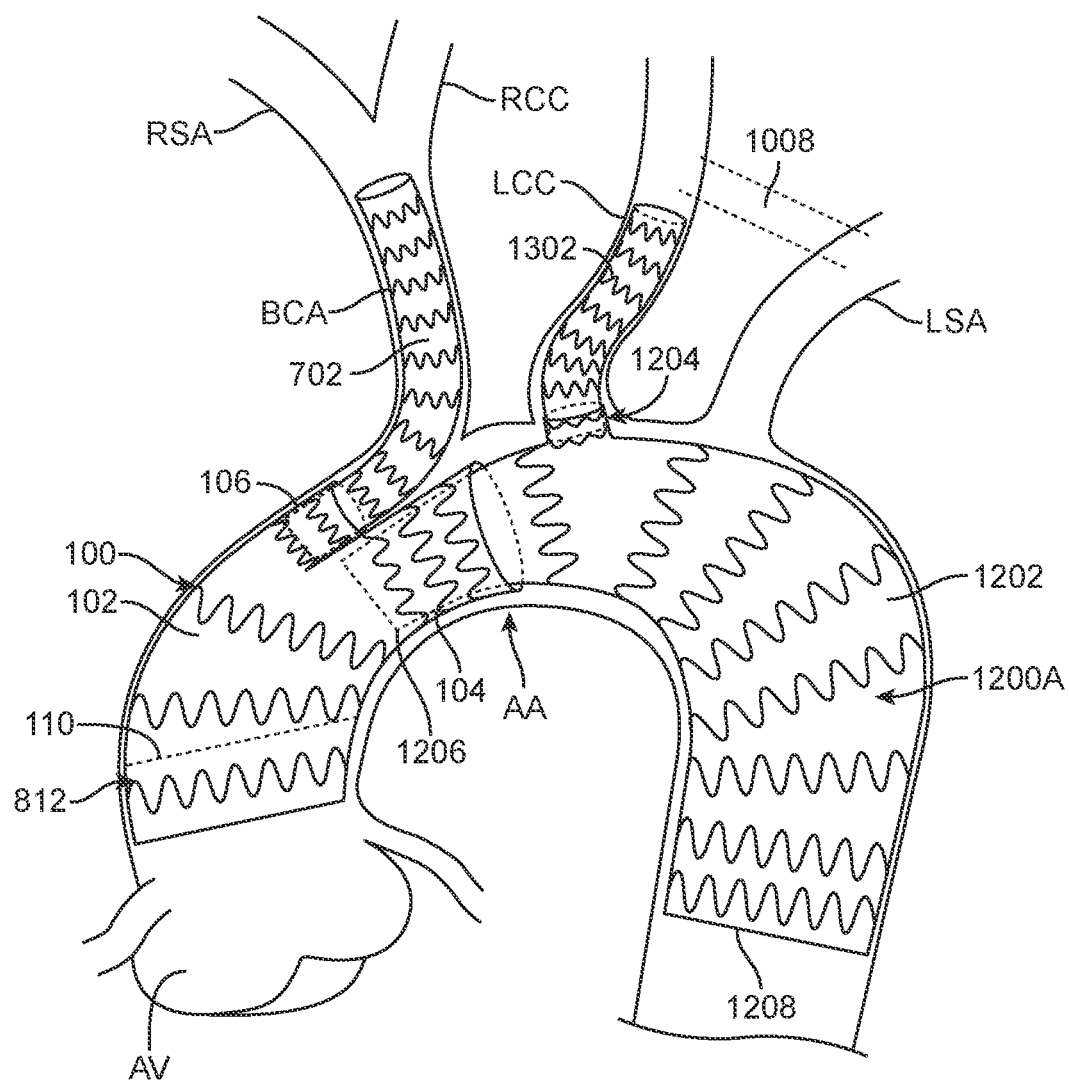
FIG. 15 is a cross-sectional view of the vessel assembly of FIG. 14 at a later stage during deployment of a bridging stent graft in accordance with one embodiment.

FIG. 14 is a cross-sectional view of vessel assembly 300 of FIG. 8 at a later stage during deployment of a distal aortic stent-graft prosthesis 1200A, sometimes called a second modular stent device 1200A, in accordance with another embodiment. FIG. 15 is a cross-sectional view of vessel assembly 300 of FIG. 14 at a later stage during deployment of bridging stent graft 1302 in accordance with one embodiment. FIGS. 14 and 15 are similar to FIGS. 12 and 13 and only the significant differences are discussed below.

In accordance with this embodiment, the positioning of coupling 1204 upon main body 1202 in aortic stent-graft prosthesis 1200A is different (more proximal) than the position of coupling 1204 upon main body 1202 in aortic stent-graft prosthesis 1200 of FIGS. 12 and 13.

Main body 1202 is deployed such that coupling 1204 is aligned with the left common carotid artery LCC in accordance with this embodiment.

Accordingly, blood flow from the lumen of main body 1202 flows through coupling 1204 and into the left common carotid artery LCC. More particularly, blood flows enter into base 1210 of coupling 1204, through the lumen of coupling 1204, and exits top 1212 of coupling 1204 into the left common carotid artery LCC.

Paying particular attention now to FIG. 15, bridging stent graft 1302 is deployed within coupling 1204 and within the left common carotid artery LCC. More particularly, bridging stent graft 1302 is anchored within coupling 1204 and the left common carotid artery LCC. Bridging stent graft 1302 is deployed via supra aortic access through the left common carotid artery LCC or alternatively through femoral access. Upon deployment of bridging stent graft 1302, blood flow into coupling 1204 is bridged and passed into the left common carotid artery LCC through bridging stent graft 1302.

In accordance with this embodiment, main body 1202 overlaps, excludes and thus occludes the left subclavian artery LSA. In accordance with this embodiment, bypass 1008 provides perfusion to the left subclavian artery LSA. Illustratively, bypass 1008 provides perfusion of the left subclavian artery LSA from the left common carotid artery LCC.

This application is related to co-filed and commonly assigned U.S. patent application Ser. No. 16/367,889, issued as U.S. Pat. No. 11,304,794 on Apr. 19, 2022, entitled "MODULAR STENT DEVICE FOR MULTIPLE VESSELS AND METHOD", of Perkins et al. and U.S. patent application Ser. No. 16/367,906, issued as U.S. Pat. No. 11,116,650 on Sep. 14, 2021, entitled "SUPRA AORTIC ACCESS MODULAR STENT ASSEMBLY AND METHOD", of Perkins et al., which are both herein incorporated by reference in their entireties.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method comprising:
    deploying a first modular stent device in an ascending portion of an aorta, the first modular stent device including:
        a first main body;
        a first bypass gate extending from a distal end of the first main body; and
        a first artery leg extending from a distal end of the first main body;
        wherein the first main body has a first longitudinal axis through a center of the first main body, the first bypass gate has a second longitudinal axis through a center of the first bypass gate, and the first artery leg has a third longitudinal axis through a center of the first artery leg, the first, second, and third longitudinal axes are parallel with one another when the first modular stent device is in a relaxed configuration;
        wherein the first artery leg is shorter than the first bypass gate;
        wherein the first main body has a first diameter, the first bypass gate has a second diameter, and the first artery leg has a third diameter, the second diameter being greater than the third diameter;
        wherein the first artery leg has a greater radial force than a radial force of the first bypass gate;
        the first bypass gate and the first artery leg are deployed in the aorta and the greater radial force of the first artery leg causes the first bypass gate to collapse preferentially to the first artery leg;
    deploying a first bridging stent graft within the first artery leg and extending into a brachiocephalic artery;
    deploying a second modular stent device in the first bypass gate, the second modular stent device including:
        a second main body;
        a second bypass gate extending from a distal end of the second main body; and
        a second artery leg extending from a distal end of the second main body;
        wherein the second main body has a fourth longitudinal axis through a center of the second main body, the second bypass gate has a fifth longitudinal axis through a center of the second bypass gate, and the second artery leg has a sixth longitudinal axis through a center of the second artery leg, the fourth, fifth, and sixth longitudinal axes are parallel with one another when the second modular stent device is in a relaxed configuration;
        wherein the second artery leg is shorter than the second bypass gate;
        wherein the second main body has a fourth diameter, the second bypass gate has a fifth diameter, and the second artery leg has a sixth diameter, the fifth diameter being greater than the sixth diameter;
    the second main body is deployed within the first bypass gate
    the second bypass gate extends past a left subclavian artery and into a descending aorta; and
    deploying a second bridging stent graft within the second artery leg and extending into a branch vessel selected from a left common carotid artery or the left subclavian artery, wherein the second bridging stent graft extends from a distal opening of the second artery leg that is located proximal to the branch vessel.

2. The method of claim 1, wherein the second bridging stent graft extends into the left common carotid artery.

3. The method of claim 2, wherein the second bridging stent graft extends into the left subclavian artery.

4. The method of claim 1 further comprising coupling a proximal cuff to the first main body.

5. The method of claim 1 wherein a radiopaque marker is coupled to the first main body and is aligned with the first artery leg.

6. The method of claim 1 further comprising controlling proximal deployment accuracy of the first main body with a tip capture mechanism.

7. The method of claim 1, wherein the first diameter is greater than the second diameter and the third diameter together at a transition region where the first main body meets the first bypass gate and the first artery leg.

8. The method of claim 1, wherein the fourth diameter is greater than the fifth diameter and the sixth diameter together at a transition region where the second main body meets the second bypass gate and the second artery leg.

9. The method of claim 1, wherein at least a portion of the second artery leg is deployed within the first bypass gate.

10. The method of claim 1, wherein blood entering the second bypass gate is discharged directly into the descending aorta.

11. The method of claim 1, wherein the first bypass gate flares to a larger diameter at a distal end thereof.

12. The method of claim 1, wherein the second bypass gate flares to a larger diameter at a distal end thereof.

* * * * *